US00PP26374P2

(12) United States Plant Patent
Shim

(10) Patent No.: US PP26,374 P2
(45) Date of Patent: Feb. 2, 2016

(54) ***HIBISCUS* PLANT NAMED 'SHIMRV24'**

(50) Latin Name: *Hibiscus syriacus*
Varietal Denomination: SHIMRV24

(71) Applicant: Kyung Ku Shim, Youngin (KR)

(72) Inventor: Kyung Ku Shim, Youngin (KR)

(73) Assignee: Spring Meadow Nursery Inc., Grand Haven, MI (US)

( * ) Notice: Subject to any disclaimer, the term of this patent is extended or adjusted under 35 U.S.C. 154(b) by 188 days.

(21) Appl. No.: 13/998,439

(22) Filed: Oct. 31, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Anne Grunberg
(74) *Attorney, Agent, or Firm* — C. A. Whealy

(57) ABSTRACT

A new and distinct cultivar of *Hibiscus* plant named 'SHIMRV24', characterized by its relatively compact and upright to outwardly spreading plant habit; vigorous growth habit; glossy dark green-colored leaves; flowers with purple-colored petals and dark red purple-colored centers and venation; and good garden performance.

2 Drawing Sheets

Botanical designation: *Hibiscus syriacus*.
Cultivar denomination: 'SHIMRV24'.

BACKGROUND OF THE INVENTION

The present invention relates to a new and distinct cultivar of *Hibiscus*, botanically known as *Hibiscus syriacus*, commercially known as Rose-of-Sharon or Althea, and hereinafter referred to by the name 'SHIMRV24'.

The new *Hibiscus* plant is a product of a planned breeding program conducted by the Inventor in Suwon, Korea. The objective of the breeding program was to develop new compact *Hibiscus* plants with attractive flowers.

The new *Hibiscus* plant originated from a cross-pollination conducted by the Inventor in July, 2002 of *Hibiscus syriacus* 'Antong Two', disclosed in U.S. Plant Pat. No. 19,547, as the female, or seed, parent with *Hibiscus syriacus* 'Busae', not patented, as the male, or pollen, parent. The new *Hibiscus* plant was discovered and selected by the Inventor in July, 2008 as a single flowering plant within the progeny of the stated cross-pollination in a controlled environment in Suwon, Korea.

Asexual reproduction of the new *Hibiscus* plant by softwood cuttings since June, 2009 in a controlled environment in Suwon, Korea has shown that the unique features of this new *Hibiscus* plant are stable and reproduced true to type in successive generations of asexual reproduction.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SHIMRV24'. These characteristics in combination distinguish 'SHIMRV24' as a new and distinct *Hibiscus* plant:

1. Relatively compact and upright to outwardly spreading plant habit.
2. Vigorous growth habit.

3. Glossy dark green-colored leaves.
4. Flowers with purple-colored petals and dark red purple-colored centers and venation.
5. Good garden performance.

Plants of the new *Hibiscus* can be compared to plants of the female parent, 'Antong Two'. Plants of the new *Hibiscus* differ primarily from plants of 'Antong Two' in flower color as plants of 'Antong Two' have white-colored flowers with red purple-colored centers and venation.

Plants of the new *Hibiscus* can be compared to plants of the male parent, 'Busae'. Plants of the new *Hibiscus* differ primarily from plants of 'Busae' in the following characteristics:

1. Plants of the new *Hibiscus* are more compact than plants of 'Busae'.
2. Leaves of plants of the new *Hibiscus* are darker green and glossier than leaves of plants of 'Busae'.
3. Petals of plants of the new *Hibiscus* are purple in color whereas petals of plants of 'Busae' are pinkish red in color.

Plants of the new *Hibiscus* can be compared to plants of the *Hibiscus syriacus* 'Minrosa', disclosed in U.S. Plant patent application Ser. No. 09/642,987 (abandoned). In side-by-side comparisons conducted in Grand Haven, Mich., plants of the new *Hibiscus* differed from plants of 'Minrosa' in the following characteristics:

1. Plants of the new *Hibiscus* were more compact than plants of 'Minrosa'.
2. Plants of the new *Hibiscus* had darker green-colored leaves than plants of 'Minrosa'.
3. Plants of the new *Hibiscus* had smaller flowers than plants of 'Minrosa'.
4. Flowers of plants of the new *Hibiscus* were flatter than flowers of plants of 'Minrosa'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet is a side perspective view of a typical plant of 'SHIMRV24' grown in a container in an outdoor nursery.

The photograph on the second sheet is a close-up view of a typical flower of 'SHIMRV24'.

DETAILED BOTANICAL DESCRIPTION

The aforementioned photographs and following observations, measurements and values describe plants grown in three-gallon containers during the spring and summer in an outdoor nursery in Grand Haven, Mich. and under cultural practices typical of commercial *Hibiscus* production. Plants were three years old when the photographs and the description were taken. In the following detailed description, color references are made to The Royal Horticultural Society Colour Chart, 1995 Edition, except where general terms of ordinary dictionary significance are used.

Botanical classification: *Hibiscus syriacus* 'SHIMRV24'.

Parentage:

*Female, or seed, parent.*—*Hibiscus syriacus* 'Antong Two', disclosed in U.S. Plant Pat. No. 19,547.

*Male, or pollen, parent.*—*Hibiscus syriacus* 'Busae', not patented.

Propagation:

*Type.*—By softwood cuttings.

*Time to initiate roots, summer.*—About four weeks at temperatures about 24° C.

*Time to produce a rooted young plant, summer.*—About six months at temperatures about 24° C.

*Root description.*—Thick, white in color.

*Rooting habit.*—Freely branching; dense.

Plant description:

*Plant and growth habit.*—Perennial deciduous shrub; relatively compact and upright to outwardly spreading plant habit; vigorous growth habit.

*Branching habit.*—Freely branching habit, usually about twelve primary branches with numerous secondary lateral branches developing per plant; pinching enhances lateral branch development.

*Plant height.*—About 42 cm.

*Plant diameter* (*area of spread*).—About 27 cm.

Lateral branch description:

*Length.*—About 34 cm.

*Diameter.*—About 3 mm.

*Internode length.*—About 3.8 cm.

*Texture, immature.*—Smooth, glabrous.

*Texture, mature.*—Woody.

*Color, immature.*—Close to 137A.

*Color, mature.*—Close to 197B.

Leaf description:

*Arrangement.*—Alternate, simple.

*Length.*—About 4.7 cm.

*Width.*—About 3.1 cm.

*Shape.*—Ovate.

*Apex.*—Acute.

*Base.*—Cuneate.

*Margin.*—Crenate.

*Texture, upper surface.*—Smooth, glabrous; luster, glossy.

*Texture, lower surface.*—Pubescent.

*Venation pattern.*—Palmate; reticulate.

*Color.*—Developing leaves, upper surface: Close to 137B. Developing leaves, lower surface: Close to 138A. Fully expanded leaves, upper surface: Close to 137A; venation, close to 136A. Fully expanded leaves, lower surface: Close to 137B; venation, close to 146D.

*Petiole.*—Length: About 2 cm. Diameter: About 1 mm. Texture, upper and lower surfaces: Smooth, glabrous. Color, upper and lower surfaces: Close to 138A.

Flower description:

*Flower appearance and arrangement.*—Single rotate flowers; flowers terminal and axillary; freely flowering habit with usually about eight flowers developing per lateral branch; flowers face upright to outwardly.

*Flower longevity.*—Flowers last for about two to three days on the plant; flowers not persistent.

*Natural flowering season.*—Plants of the new *Hibiscus* flower continuously throughout the summer in Michigan.

*Flower diameter.*—About 7 cm.

*Flower length* (*height*).—About 3.5 cm.

*Flower buds.*—Length: About 1.2 cm. Diameter: About 7 mm. Shape: Ovate. Color: Close to 143C.

*Petals.*—Arrangement and quantity: Single whorl of five petals; petals imbricate. Length: About 4 cm. Width: About 2.4 cm. Shape: Obovate. Apex: Acute, reflexed. Base: Attenuate. Margin: Entire. Texture, upper and lower surfaces: Rugose, glabrous. Color: When opening, upper surface: Blend of close to 66A and 78A; towards the base and venation, close to 59B. When opening, lower surface: Blend of close to 66B and 78B. Fully opened, upper surface: Blend of close to 66A and 78B; towards the base and venation, close to 59B. Fully opened, lower surface: Blend of close to 66C and 78D. Throat: Close to 59A to 59B. Tube: Blend of close to 66C and 78D.

*Sepals.*—Arrangement and quantity: Single whorl of five sepals fused into a tubular calyx. Length: About 1.5 cm. Width: About 5 mm. Shape: Subulate. Apex: Acuminate. Margin: Entire. Texture, upper and lower surfaces: Smooth, glabrous. Color, when opening and fully opened, upper surface: Close to 145B; towards the base, close to 143B. Color, when opening and fully opened, lower surface: Close to 145A.

*Peduncles.*—Length: About 2.5 cm. Diameter: About 4 mm. Strength: Strong. Texture: Smooth, glabrous. Angle: About 30° to 50° from the stem axis. Color: Close to 143B.

*Reproductive organs.*—Androecium: Quantity per flower: About 35. Anther shape: Round. Anther length: About 2 mm. Anther color: Close to 2D. Amount of pollen: Abundant. Pollen color: Close to 10C. Gynoecium: Quantity per flower: One. Pistil length: About 4 cm. Style length: About 3.2 cm. Style color: Close to 2D. Stigma appearance: Five-parted, rounded. Stigma color: Close to 2D. Ovary color: Close to 4D.

*Seeds and fruits.*—Seed and fruit development have not been observed on plants of the new *Hibiscus*.

Garden performance: Plants of the new *Hibiscus* have been observed to have excellent garden performance and to tolerate rain, wind and temperatures ranging from about −20° C. to about 43° C.

Pathogen & pest resistance: Plants of the new *Hibiscus* have not been shown to be resistant to pathogens and pests common to *Hibiscus* plants.

It is claimed:

1. A new and distinct *Hibiscus* plant named 'SHIMRV24' as illustrated and described.

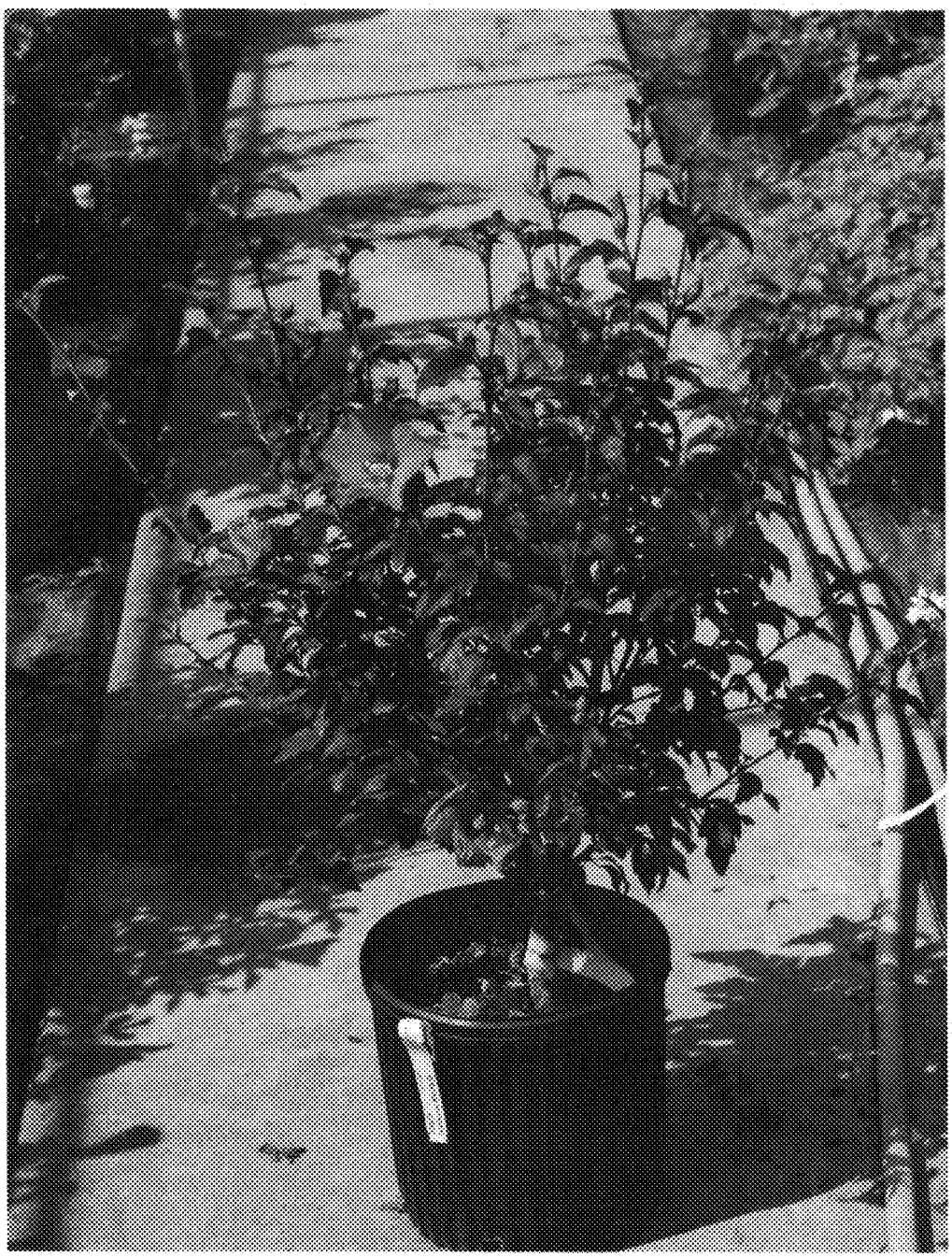

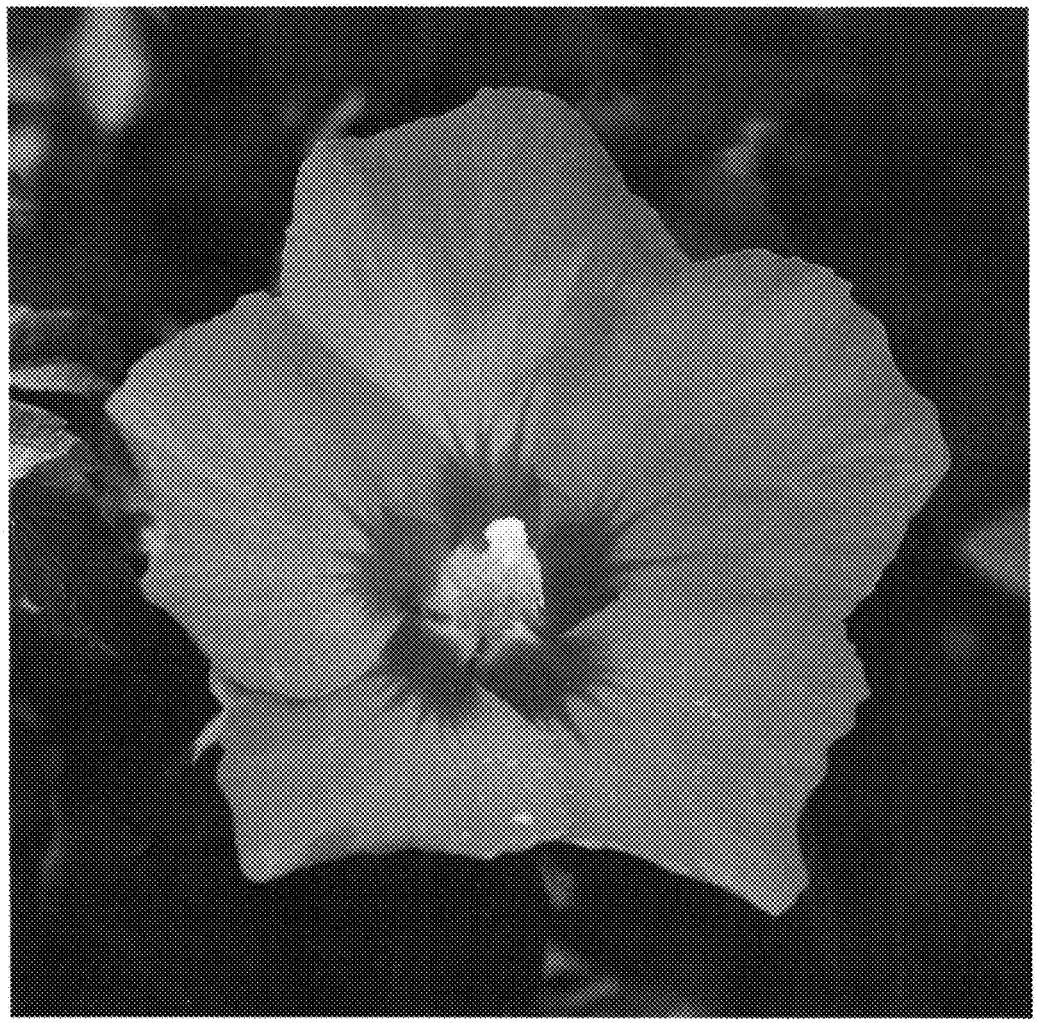

* * * * *